(12) United States Patent
Roesler

(10) Patent No.: US 9,999,469 B2
(45) Date of Patent: Jun. 19, 2018

(54) PACKAGE FOR ELONGATED SHARP-EDGED TOOLS

(71) Applicant: Peter Roesler, Wangen (DE)

(72) Inventor: Peter Roesler, Wangen (DE)

(73) Assignee: Rose Plastic AG (DE)

( * ) Notice: Subject to any disclaimer, the term of this patent is extended or adjusted under 35 U.S.C. 154(b) by 0 days. days.

(21) Appl. No.: 14/202,344

(22) Filed: Mar. 10, 2014

(65) Prior Publication Data

US 2014/0251846 A1    Sep. 11, 2014

(30) Foreign Application Priority Data

Mar. 9, 2013    (DE) .................. 10 2013 004 146

(51) Int. Cl.
*A61B 19/02*    (2006.01)
*A61B 50/30*    (2016.01)
*A61B 50/00*    (2016.01)

(52) U.S. Cl.
CPC ............ *A61B 19/026* (2013.01); *A61B 50/30* (2016.02); *A61B 2050/0057* (2016.02); *A61B 2050/0083* (2016.02)

(58) Field of Classification Search
CPC ... A61B 19/02; A61B 19/026; A61B 17/3215; A61B 2019/021; A61B 2019/0239; B65D 43/161

See application file for complete search history.

(56) References Cited

U.S. PATENT DOCUMENTS

| 4,619,364 | A | * | 10/1986 | Czopor, Jr. ............ B65D 85/20 206/379 |
| 4,736,842 | A | * | 4/1988 | Uetake et al. ................ 206/363 |
| 4,998,334 | A | * | 3/1991 | Pemberton ......... A61B 17/3217 206/359 |
| 5,088,173 | A | * | 2/1992 | Kromer et al. ................. 29/239 |
| 5,090,564 | A | * | 2/1992 | Chimienti ........... A61M 5/3205 206/365 |
| 5,407,066 | A | * | 4/1995 | Grange .................. A45D 27/29 206/228 |
| 5,433,321 | A | * | 7/1995 | Abidin et al. ................ 206/354 |
| 6,152,299 | A | * | 11/2000 | O'Malley .............. B65D 75/22 206/349 |
| 6,629,985 | B1 | * | 10/2003 | Kiehne ......................... 606/167 |
| 6,634,503 | B2 | * | 10/2003 | Welsh, Jr. ..................... 206/553 |

(Continued)

FOREIGN PATENT DOCUMENTS

DE    202005007589         7/2005
DE    202005007586 U1     9/2005

(Continued)

*Primary Examiner* — Anthony Stashick
*Assistant Examiner* — James Way
(74) *Attorney, Agent, or Firm* — Cohen & Grigsby, PC

(57) ABSTRACT

Package for elongated sharp-edged objects, in particular for tools useful for surgical applications, which are secured in a fixed position in a package consisting at least partially of plastic, wherein the package comprises an a first enlarged package part which defines an interior into which the object that is to be protected and secured protrudes with its sharp edges in a noncontact manner and a second package part in which the shaft of the object is accommodated and held in a fixed position by holding elements.

13 Claims, 5 Drawing Sheets

(56) References Cited

U.S. PATENT DOCUMENTS

| | | | |
|---|---|---|---|
| 7,434,684 B1 * | 10/2008 | Mabra | F41B 5/14 |
| | | | 206/315.11 |
| 2006/0157363 A1 | 7/2006 | Abidin et al. | |
| 2009/0259241 A1 * | 10/2009 | Nakamura | 606/167 |
| 2010/0111759 A1 | 5/2010 | Smith et al. | |

FOREIGN PATENT DOCUMENTS

| | | |
|---|---|---|
| DE | 202010005089 | 7/2010 |
| DE | 202010005089 U1 | 8/2010 |
| EP | 1961390 | 8/2008 |
| EP | 1961390 A1 | 8/2008 |
| EP | 2236105 | 10/2010 |
| EP | 2236105 A1 | 10/2010 |

* cited by examiner

PACKAGE FOR ELONGATED SHARP-EDGED TOOLS

BACKGROUND

1. Technical Field of the Invention

The invention relates to a package for elongated sharp-edged tools. More specifically, the invention relates to a package for storage of precision tools which have a sharp-edged working surface in at least one location and which must be protected from contact with the material of the package.

2. Description of the Related Art

The presently disclosed invention is described in connection with a surgical instrument such as an oscillating saw or a bone saw or the like is assumed as an example of a surgical instrument. The description of an oscillating saw with a sharp-edged serrated blade is only as an example without limiting the scope of the invention.

In packaging such surgical instruments, there is the problem that the blade, cutting edge, or other sharp-edged working surface must not come in contact with the material of the package, which is preferably made of plastic. This situation has been remedied in the past by welding such a sharp-edged tool in various film layers for packaging purposes, thus accepting the disadvantage of the risk that in shipping and storage of such a packaged object, the sharp-edged blade or the cutting edge may unintentionally come in contact with the plastic of the packaging film. When the object packaged in this way was removed from the package, there was the risk of microtine plastic particles from the package adhering to the serrated cutting edge of the tool. In a subsequent surgical operation, there was then the risk that the plastic particles adhering to the cutting surface would penetrate into the surgical wound. Likewise, there was a substantial risk of injury when the surgeon would grip the blade of the surgical instrument, which was packaged only in the film bag, to liberate it from the package and clamp it in a machine.

The object of the presently disclosed invention is therefore to create a package for a sharp-edged object, such as a tool useful for medical purposes, that will ensure that its cutting edge or sawing edge will not come into contact with any surface of the package. It is a further object of the presently disclosed invention to provide packaging which may ensure that the object can be removed from the package easily, reliably and without either contamination or injury.

SUMMARY

The presently disclosed invention overcomes many of the shortcomings of the prior art by providing a sterile package which may maintain the sharp edges of a surgical tool in a first package portion in a non-contact manner and the surgical tool shaft in a second package portion held in a fixed position by holding elements. The package includes an enlarged first package area which defines an interior into which an object to be protected and held protrudes with its cutting or milling surfaces making no contact with any portion of the package, and the shaft of the object accommodated in a second package area, where it is held in a fixed position with the help of holding elements when the package is closed.

The presently disclosed invention is thus a package consisting of at least two regions or parts a front part with a larger chamber volume, into which the cutting or milling edges of the object to be secured protrudes and are maintained at a distance on all sides from the surrounding package surfaces, and a holding part which secures the remaining portion of the object to be held, generally the shaft or handle, in a fixed position.

Because the package is divided into at least two regions, there is the advantage that the front portion of the object to be held protrudes freely into the front part of the package where it does not come in contact with any package walls and consequently may not be contaminated by the walls of the package. Further, the shaft portion of the object to be secured is held in the holding part of the package under the influence of elastically deformable holding elements, making removal of the shaft portion safer for the surgeon.

While the presently disclosed invention is described in the following three embodiments, it should be appreciated that various modifications and alterations and applications could be developed in light of the overall teaching of this disclosure.

Provided in one embodiment is a protective package includes a bottom part, which is pivotably connected to a top part by means of a pivot axis running parallel to the longitudinal extent of the package. The pivotable connection between the top part and the bottom part is formed by a film hinge arranged laterally between the two parts, for example. The two parts (top part and bottom part) are thus pivotably connected to one another along the longitudinal side by the film hinge and can be sealed to one another on the opposite side by a snap lock. A commercial pivot hinge may also be used instead of a film hinge.

For packaging an object in such a package, the object is first placed in a cleanroom, where it is cleaned under cleanroom conditions. The object is then combined with the package according to the invention to provide protection (protective package).

For insertion of the object into the protective package, the two parts of the package are opened and the object to be secured is placed in the bottom part in such a way that the rear portion of the object (shaft) to be secured rests on holding elements in a holding part of the bottom part of the package. The package is then closed by pivoting the top part down onto the bottom part and locking the two parts together.

After the object to be protected has been inserted into the protective package under cleanroom conditions, in another process step, the protective package completed in this way is inserted, together with the object accommodated therein, into a second package which is subsequently sealed under cleanroom conditions. The second package may be designed as a polybag.

Elastically deformable holding elements may be arranged on the top part, cooperating with holding elements arranged in the bottom part, so that the shaft part of the object to be retained is held in a secured position in the two-part package by the elastomerically deformable holding elements. It is also sufficient to mount the holding element or elements alone in the top part or in the bottom part of the package. However, it is preferable if the elastomerically deformable holding elements are arranged opposite one another and aligned with one another on the top part as well as on the bottom part to form a clamping face for the shaft of the object to be held there between.

In embodiments, the elastomerically deformable holding elements may consist of an elastically deformable face, which is smooth and without holding nubs and exerts a holding force on the shaft of the object through elastic deformation alone, without any other protrusions. The holding force thus depends on the locking force of the two package parts to one another. The locking force may preferably be designed to be adjustable.

In another embodiment, it may be provided that the elastomerically deformable holding elements form a surface profile consisting of nubs, tips, strips or wavy corrugations, for example. To open such a package, the snap lock is simply opened and the top part is pivoted away from the bottom part, so that the object can be removed easily from the package.

In the one embodiment, the holding part of the package configured for holding the shaft of the object is designed in one piece with the package. In another embodiment of the presently disclosed invention, the holding part of the package, which is provided for holding the shaft of the object, may be designed in at least two parts. The front part of the holding part (shaft part) of the package may be designed as a clamping part according to the first embodiment, whereas the rear portion of the holding part may be designed as a flap part. The flap part may be connected to the front part of the holding part, namely the shaft part, by means of a bending edge. If the two parts of the flap part are pivoted away from one another, then the rear part of the shaft of the object becomes free and the object can be removed after opening the top part and the bottom part.

In still another embodiment of the presently disclosed invention, it is provided that the package with the holding part is designed to be so short that the object with its shaft part protrudes out of the protective package toward the rear. This is advantageous in particular with objects or tools having a very long shaft, the length of which is greater than the length of the protective package.

A combination of the three embodiments mentioned above is of course also possible, so that with the embodiment mentioned last, for example, it may also be provided that the two package parts (top part and bottom part) are designed to be pivotable toward one another.

In all the embodiments, it is thus important that the package consists of at least two areas in the direction of the longitudinal extent of the object to be held, namely a front part with a relatively large accommodation volume into which the object to be held protrudes with its sensitive cutting surfaces or milling surfaces in a free-standing accommodation, so that these surfaces do not come in contact with the wall of the package at any point. The second region of the package is designed as a holding part, which serves to hold the rear part (shaft part) of the object to be secured. It is preferable here if the object to be secured is held with elastomerically deformable holding elements, although the invention is not limited to this form. The holding elements are either large-area holding faces, whose area extent exceeds the area of the face of the object to be secured, or these may be small-area holding faces whose area extent is smaller than the area of the object to be secured.

All the information and features disclosed in the patent documents, including the abstract, in particular the three-dimensional design depicted in the drawings, are part of the invention inasmuch as they are novel individually or in combination in comparison with the prior art.

BRIEF DESCRIPTION OF THE DRAWINGS

The presently disclosed invention is explained in greater detail below on the basis of drawings, which illustrate only one method of implementation. The drawings and their description show additional features and advantages of the invention, wherein.

DETAILED DESCRIPTION

Figure 1:
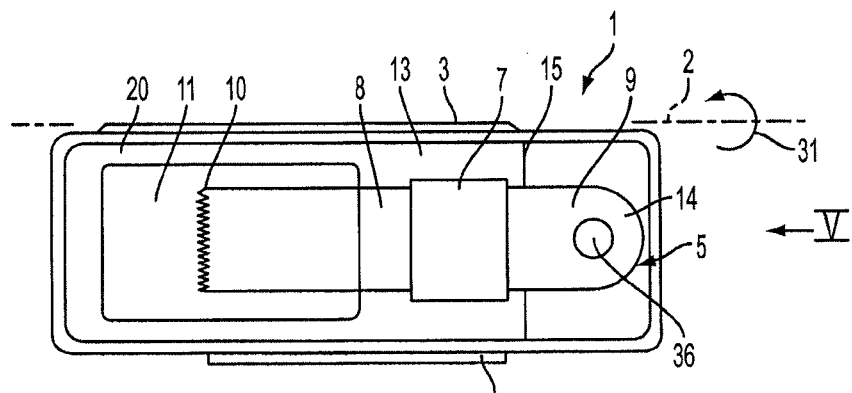
FIG. 1 illustrates a top view of a first embodiment of a package in a closed state.
Figure 2:
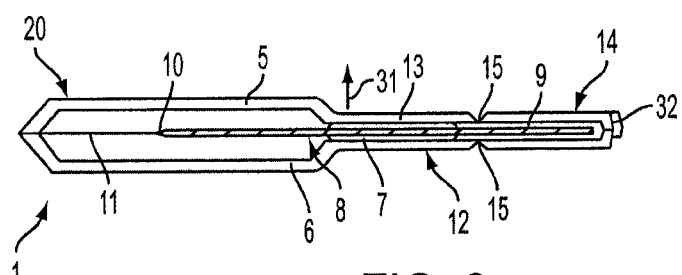
FIG. 2 illustrates a longitudinal section through the package according to FIG. 1.
Figure 3:
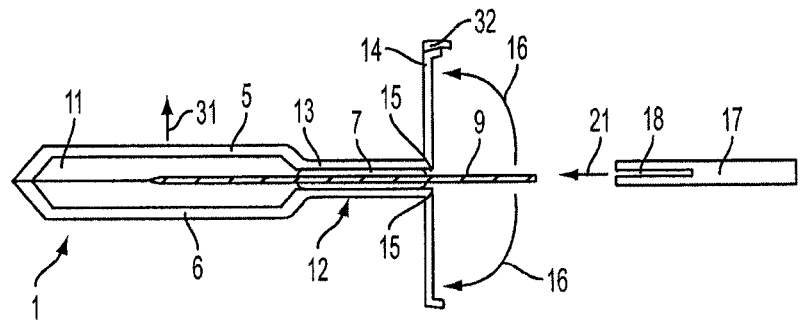
FIG. 3 illustrates the package from FIG. 2 with the flap part opened.
Figure 4:
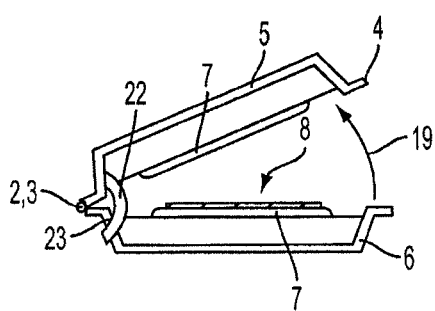
FIG. 4 illustrates a side view of the package according to FIG. 1 in a partially opened condition, showing additional details.

FIGS. 1 and 2 as well as FIGS. 3 and 4 show a first embodiment of a package that includes a top part 5, which may be pivotably connected to a bottom part 6 by a lateral pivot axis 2 and a film hinge 3 arranged therein. The pivot axis 2 is shown with dashed lines in FIG. 1, where it can be seen that the top part 5 may be designed to be pivotable with respect to the bottom part 6 in the direction of the arrow 31. A snap lock 4 may be arranged opposite the pivot axis 2 between the top part and the bottom part (5, 6), so that the two package parts (5, 6) can be releasably locked together by means of the snap lock 4.

Figure 5:
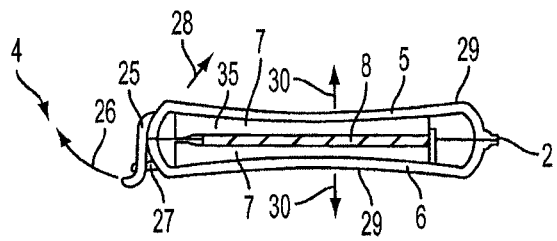
FIG. 5 illustrates a sectional view of the package according to FIG. 1 or 8.

FIG. 5 shows as an exemplary embodiment of a snap lock an opening strap 25, which may be attached in a flexible, elastic manner to the one side of the top part 5 and may engage in the locked condition through a latch 27 situated on the bottom part 6. The opening strap 25 may be operated in the direction of the arrow 26, so that the top part 5 can be pivoted upward in the direction of the arrow 28 away from the bottom part 6 in the pivot axis 2.

Figure 4A:
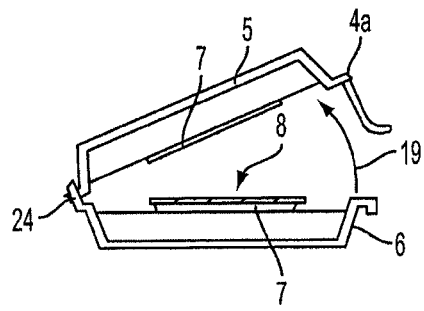
FIG. 4a illustrates a second embodiment in comparison with FIG. 4.

Instead of a snap lock 4, all other releasable closures may of course also be used such as, for example, pushbuttons, hook-and-loop closures, magnetic closures or closures, in which tooth elements in the form of rows of teeth oriented in the longitudinal direction engage with a protrusion engaging in the rows of teeth. Such a snap lock with intermeshing rows of teeth is illustrated in the exemplary embodiment according to FIG. 4a. Furthermore, FIG. 4a shows that in comparison with FIG. 4, a pivot bearing 24 may be formed by the fact that the top part 5 engages with a protruding journal in a respective slot-shaped receptacle in the bottom part 6, thereby forming a pivot bearing.

FIG. 4 shows a means of securing the film hinge 3, such that a securing strap 22 which engages with its free lower end in a recess 23 provided in the bottom part 6 may be arranged on the top part. Thus, there is an additional securing device for the film hinge 3. Likewise the load on the film hinge 3 can be relieved by this securing strap 22.

The presently disclosed invention is of course not limited to the arrangement of a securing strap 22 on the top part and conversely in the arrangement of a recess 23 in the bottom part. All the aforementioned embodiments, as well as the embodiments to be mentioned later, also function in a kinematic inversion. Consequently, the terms "top part 5" and "bottom part 6" as well as all the mutually supplementing parts mentioned in this context are to be understood as interchangeable and having equivalent meanings.

The package 1 may consist essentially of two regions in the direction of the longitudinal extent of an object 8 to be secured: a front part 20 with an interior 11 having a larger volume in comparison with the volume of the object protruding therein, and a smaller holding part 12 which is smaller by comparison and is suitable for accommodating the shaft 9 of the object 8 that is to be secured in a frictionally engaged manner.

Figure 17:
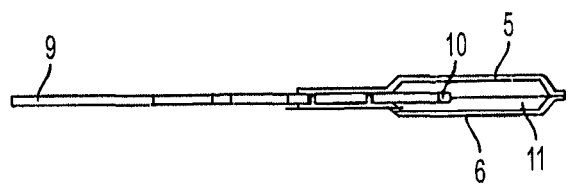
FIG. 17 illustrates the position of the object according to FIG. 16 secured in the package.
Figure 18:
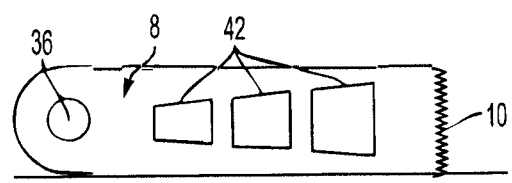
FIG. 18 illustrates a top view of an object in another embodiment with the recesses provided therein.
Figure 19:
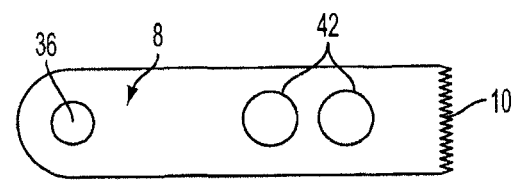
FIG. 19 illustrates an embodiment of an object modified in comparison with FIG. 18.

In addition to this friction-locking method of securing the shaft 9 of the object 8 to be secured, additional form-fitting connections may also be provided, holding the object 8 in a form-fitting manner at additional locations, such as the recesses according to FIGS. 17 to 19, for example.

In the exemplary embodiment shown herein according to FIGS. 1 and 2, the holding elements 7, which are opposite one another on the inside of the top part 5 and on the inside of the bottom part 6, and are shown as elastomerically deformable plastic ribs or sheets, may be in one piece with the material and may be connected to the plastic of the top part 5 and the bottom part 6 of the package. In embodiments, this is a two-component material formed from different soft plastic components. Consequently, the retaining elements may consist of a TPE (thermoplastic elastomer), for example, while the other parts of the package 1 may consist of a polypropylene suitable for a film hinge.

FIGS. 4 and 4a show that the object 8 may be exposed when the two package parts (5, 6) are flipped open and the object can thus be gripped by its shaft, for example, and removed. However, this type of packaging prevents any contact of the sharp-edged blade with the surfaces of the interior 11. The object can be gripped only by the shaft.

It is important that the dimensions of the interior 11 have been selected to be so large in comparison with the dimensions of the object protruding into it that the blade 10 of the object 8 to be secured is kept free of any contact with the surfaces of the interior 11. Thus, the blade 10 protrudes into the interior 11 in a free-standing accommodation without there being any risk that it will come into contact with any surface of the interior 11, even if the package is displaced sharply, such as if the package falls to the ground.

FIG. 3 shows as another exemplary embodiment that the package 1 may be formed by two regions and consist of a bottom part 6 which is connected to a top part 5 by a pivot axis 2. The package may also consist of more than two regions or two parts. In the exemplary embodiment shown according to FIG. 3, the two parts (5, 6) are pivotably joined together and the holding part 12 of the package is additionally designed in two parts and consist of a shaft part 13 and rear flap part 14 connected to it by a bending edge 15.

The elastomerically deformable holders 7 are arranged in the shaft part 13, and the flap part 14 consists of two parts that can be flipped oppositely from one another in the direction of the arrow 16 by means of bending edges 15, which can be folded up according to FIG. 3 to thereby expose the shaft 9 of the object 8 being secured, so that the slot 18 of a tool receptacle 17 may be inserted through the coupling opening 36 in the direction of arrow 21 and can be locked in place there.

In order to prevent the blade 10 from coming in contact with plastic parts in the securing part 12, it is provided that the two package parts (5, 6) are connected to one another so they can be pivoted in the pivot axis 2. On opening the package by pivoting it in the pivot axis 2, the object 8 to be protected may be completely exposed and can be removed without coming in contact with a package surface. The protective package is thus removed from the object to be protected without coming in contact with it, which is gripped by its shaft.

In all embodiments, it is important that the blade 10 of the object 8 is protected from contact with parts of the package 1. There is no risk of injury to the blade or shape edge of the object or to the person removing the object from the package. This is true in particular of the embodiment according to FIG. 3 and FIG. 8 because the shaft 9 of the object 8 to be secured is already freely accessible therein and can be easily removed without any risk of contact between the sensitive blade 10 of the object 8 and the package material. In these embodiments, the additional flap part 14 is omitted because the shaft 9 may be longer than the length of the package.

The package 1, with its snap lock 4, may be designed so that it can also be operated easily with surgical gloves.

Figure 6:
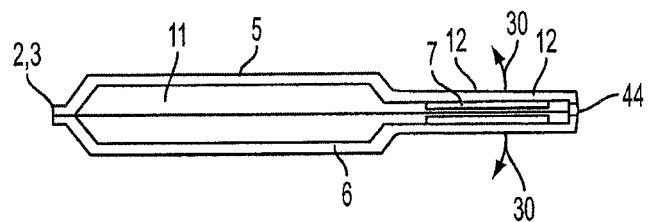
FIG. 6 illustrates a longitudinal section through a package according to FIG. 8.

FIG. 4a also shows another embodiment of a snap look which consists of intermeshing sawtooth-like protrusions that can be locked together in any position in height (or a closing position). In this case the film hinge 3 may extend in the direction of the transverse extent of the package 1. This is illustrated in FIG. 6.

Figure 5A:
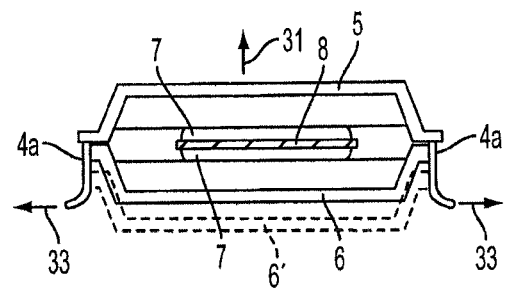
FIG. 5a illustrates an embodiment that has been modified in comparison with FIG. 5.

FIG. 5a shows as another embodiment that snap locks 4a may also be arranged on both sides to design the interior volume of the package and thus also the pressing force in the holding part 12 to be adjustable with respect to the holding elements 7 arranged there. In other words, if the top part 5 is moved in the opposite direction from the direction of the arrow 31 shown here with respect to the bottom part 6, then the snap lock 4a arranged on the left side and on the right side may be adjusted accordingly, so that the package volume is increased or decreased. Accordingly, the pressing force of the holding elements 7 on the shaft 9 of the object 8 to be held is designed to be adjustable—see the position 6' of the bottom part.

FIG. 5 shows as another embodiment that the pressing force of the holding elements 7 can also be achieved by a convex shape and a resulting prestress on the two package parts (5, 6).

The two parts (5, 6) can be produced by the injection molding process, so that they naturally have a convex shape, which results in the holding elements 7 being provided with a bias in the top part 5 and the bottom part 6 (more precisely in the holding part 12). The bias force on the holding elements 7 can thus be prestressed through the shaping of the plastics comprising the top part and the bottom part.

Figure 8:
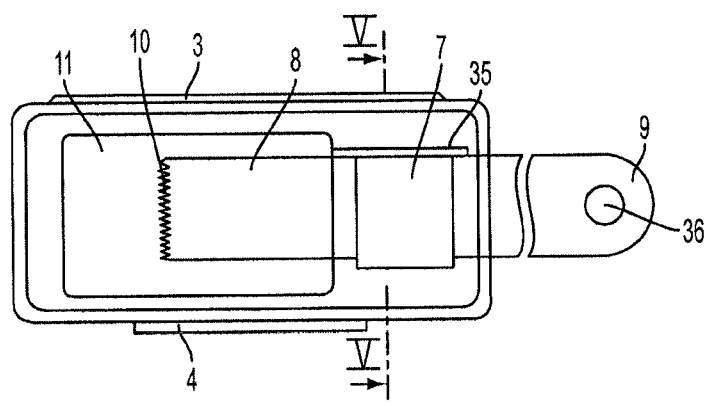
FIG. 8 illustrates a top view of the arrangement according to FIG. 7.

In addition, FIG. 5—in combination with FIG. 8—shows that a stop edge 35 running in the longitudinal direction and orienting the object 8 to be secured is provided on one or both ends, each in the region of the shaft 9 of the object 8 to be secured, namely in the region of the holding part 12. Such a stop edge 35 may also be arranged on the opposite end. This is also discernible in the section of view according to FIG. 5.

It is also indicated there that the two package parts may be pre-stressed against one another in the direction opposite the direction of the arrow 30. It is also possible that the curved shape 29 is provided only in the holding part 12 of the package 1 and that the other package parts, in particular the package parts which form the interior 11, do not have such a curved shape.

FIG. 2 also shows that the two package parts may furthermore have a locking hook 32 instead of a snap lock, so that the two package parts according to FIG. 2 are releasably connected to one another in the hold part 12 by the locking hooks 32.

FIG. 5a shows that the snap lock 4a, which consists of the saw-tooth intermeshing protrusions, can be opened in the direction of the arrow 33, so that suitable gripping are also arranged on the bottom side of the snap locks 4, 4a.

All the figures also show a plane of separation 34 between the top part 5 and the bottom part 6.

Figure 7:
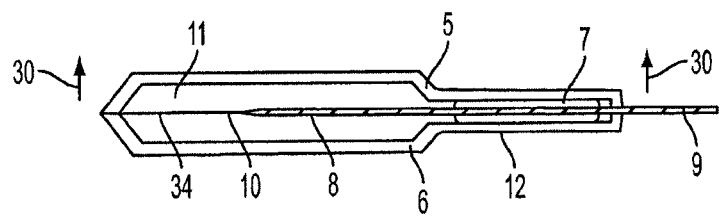
FIG. 7 illustrates the package according to FIG. 6 with the object inserted there according to a longitudinal section through FIG. 8.

The embodiment according to FIGS. 6 to 8 shows another implementation of the presently disclosed invention in which the package length is shorter than the length of the object to be secured. The object 8 to be secured protrudes out of the holding part 12 of the package 1 with its shaft 9 in the packaged state according to FIG. 7. The two package parts (5, 6) may be pivotable or can be connected to one another in a releasable manner in general to remove one part, for example, to remove the top part 5 from the bottom part 6.

FIG. 8 shows an embodiment in which the two package parts (5, 6) are pivotably connected to one another by means of the film hinge 3 along a longitudinal edge and are assigned to this pivot axis 2 opposite the snap lock 4.

Figure 9:
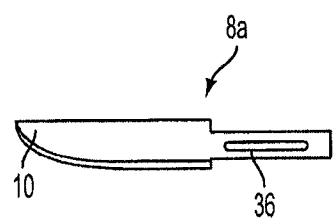
FIGS. 9 and 10 illustrate the diagram of different objects held in the package.
Figure 10:
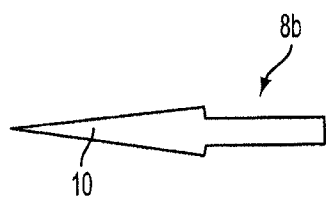

FIGS. 9 and 10 show a variety of instruments and objects 8a, 8b, indicating that the blades 10 of the objects 8a, 8b to be protected can lie in different positions and it is still always ensured that the sensitive blades 10 protrude into the front part 20 of the package 1 without coming into contact with any surfaces. The two package parts (5, 6) may be opened in the direction of the arrow 19 and are closed in the opposite direction (see FIGS. 4 and 4a).

FIGS. 11 to 15 illustrate different surface profiles 37, 38, 39, 41 of holding elements 7, which may be arranged in the holding part 12 of the package 1, shown in views from above and from the front.

Figure 11:
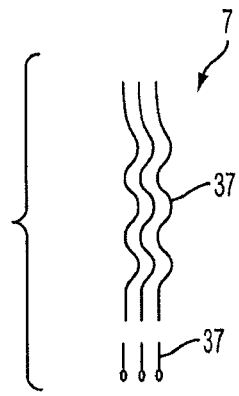
FIG. 11 illustrates the frontal view and top view through a surface profile of a first embodiment of a holding element.

FIG. 11 shows a surface profile 37 consisting of individual waves forming upwardly directed tips, so that the shaft 9 of the object to be secured can yield and deform elastically and comes to lie in contact with both sides of the shaft 9 under elastic deforming force.

Figure 12:
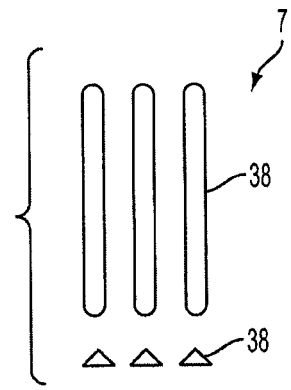
FIG. 12 illustrates a top view and a frontal view of a second embodiment of a holding element.

FIG. 12 shows instead of the wavy surface profile 37 a rib-shaped surface profile 38 which is rounded in the direction of the shaft to be secured, so that only the small radii of the surface profile pointing upward are in contact with the bottom side or the top side of the shaft 9 of the object 8.

Figure 13:
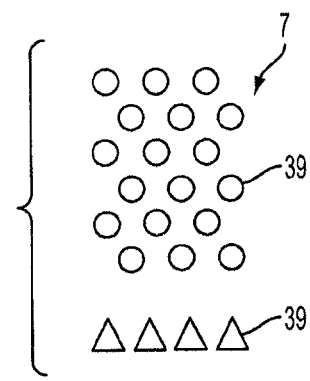
FIG. 13 illustrates a top view and a frontal view through a third embodiment of a holding element.

FIG. 13 shows a modification of a surface profile 39 which consists of individual holding tips which are profiled to be approximately triangular or half-round.

Figure 14:
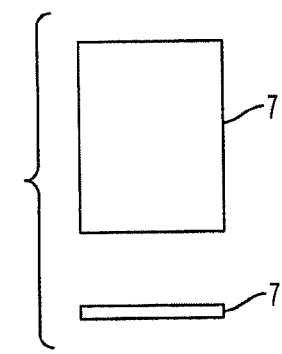
FIG. 14 illustrates a top view and a frontal view through a holding element according to FIG. 1.

FIG. 14 shows a surface profile of a holding element which is also illustrated in FIGS. 1 through 5.

Figure 15:
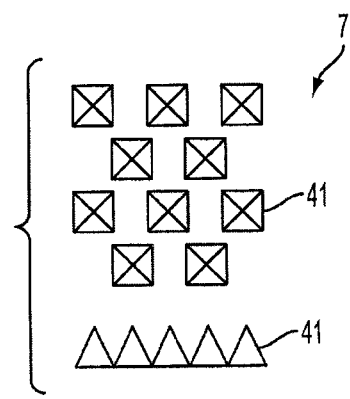
FIG. 15 illustrates a top view and a frontal view through a fourth embodiment of a holding element.
Figure 16:
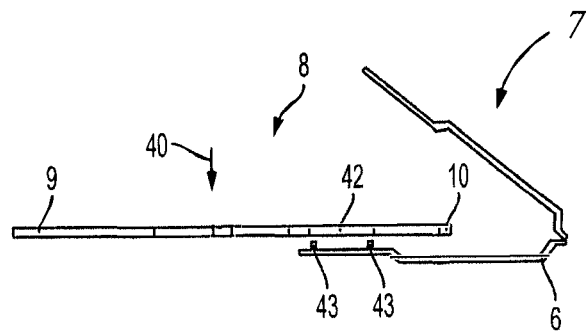
FIG. 16 illustrates a mounting position for introducing the object into the package with additional holding nubs.

FIG. 15 shows as another embodiment a surface profile 41 consisting of rectangular holding tips.

Instead of the embodiments shown here, other elastomerically deformable holding elements with different surface profiles 37-39 and 41 may also be used. The surface profiles shown in the drawings in FIGS. 11 through 15 may also be combined.

As another exemplary embodiment, FIGS. 16 through 19 show an additional form-fitting means of securing the object to be held. In the package, for example, in the top part 5 and/or in the bottom part 6, additional holding nubs 43, which engage in recesses 42 on the object 8 are provided. The shape of the holding nubs 43 may be adapted to the shape of the recesses 42, such that different shapes of recesses 42 are illustrated in FIGS. 18 and 19. The recesses 42 need not necessarily be located in the shaft area of the object to be secured but may also be arranged in other areas of the object 8 to be secured.

Therefore, a form-fitting receptacle in the holding nubs 43 may additionally be combined with the elastomerically deformable holding elements 7 in the holding part 12 by engagement in the recesses 42. In another embodiment, the elastomeric holding elements 7 in the holding part 12 may also be omitted entirely and instead only the form-fitting holding elements which are shown in FIGS. 16 to 19 and hold in a form-fitting manner the object that is to be secured at any location outside of the sensitive blade 10 in the package and only these are present here.

Such a form-fitting holder is used in particular when the length of the object to be secured is greater than the package length, for example, as illustrated in FIGS. 6 and 7. In this exemplary embodiment, the shaft 9 protrudes through a slot 44 on the rear side of the holding part 12 of the package 1.

Instead of the holding elements 7 shown there, the form-fitting holding elements may also be used with the holding nubs 43 according to FIGS. 16 to 19.

It is thus important that the holding nubs 43 are in form-fitting contact with the inside walls of the recesses 42 and that a form-fitting contact is ensured. It is not necessary for the holding nubs 43 to lock in the recesses 42 although this is also possible.

LEGEND TO THE DRAWINGS

1 Package
2 Pivot axis
3 Film hinge
4 Snap lock (with 25)
4a Snap lock (sawtooth)
5 Top part
6 Bottom part 6'
7 Holding element TPE
8 Object 8a, 8b
9 Shaft (of 8)
10 Blade (of 8)
11 Interior (of 1)
12 Holding part (consisting of 13 and 14)
13 Shaft part
14 Flap part
15 Bending edge
16 Direction of arrow
17 Tool receptacle
18 Slot
19 Direction of arrow
20 Front part (of 1)

21 Direction of arrow
22 Securing strap
23 Recess
24 Pivot bearing
25 Opening strap
26 Direction of arrow
27 Latch
28 Direction of arrow
29 Curved shape
30 Direction of arrow
31 Direction of arrow
32 Locking hook
33 Direction of arrow
34 Plane of separation
35 Stop edge
36 Coupling opening
37 Surface profile (of 7)
38 Surface profile
39 Surface profile
40 Direction of arrow
41 Direction of arrow
42 Recess
43 Holding nub
44 Slot

What is claimed is:

1. A package for securing an elongated object that has one portion with sharp edges and that also has other portions that do not have sharp edges, the package comprising:
  a first package part with surfaces that define an interior chamber having dimensions that are larger than the dimensions of the one portion of said elongated object with sharp edges, said interior chamber of said first package part receiving all of said sharp edges of said elongated object at times when said elongated object is secured in said package such that said surfaces that define said interior chamber of said first package part are spaced apart from all of said sharp edges of said elongated object; and
  a second package part that receives other portions of said elongated object that do not have sharp edges at times when said elongated object is secured in said package, said second package part defining a smaller volume than said first package part and including at least one holding element, said second package part defining a surface that is convex with respect to said at least one holding element such that said second package part biases said at least one holding element against said other portions of said elongated object at times when said elongated object is secured in said package such that said at least one holding element secures, in a fixed position and in a friction-locking manner and/or a form-fitting manner, at least a portion of said elongated object that does not have sharp edges.

2. The package according to claim 1, wherein the at least one holding element is elastically deformable.

3. The package according to claim 1, wherein the first package part in combination with the second package part comprise a bottom part, a top part, and a film hinge that pivotally connects said top part to said bottom part.

4. The package according to claim 3 wherein said package defines a pivotal axis and wherein said film hinge is arranged parallel to said pivotal axis.

5. The package according to claim 3 wherein said package defines a pivotal axis and wherein said film hinge is arranged perpendicular to said pivotal axis.

6. The package according to claim 3 further comprising one or more snap locks that releasably connect the top part to the bottom part.

7. The package according to claim 3, wherein said at least one holding element is elastically deformable.

8. The package according to claim 7, wherein at least one holding element is included in at least one of the top part and the bottom part, said at least one holding element securing the object at times when the top part and bottom part are folded together and locked to each other.

9. The package according to claim 1, wherein the second package part comprises two segments that are adapted to receive said elongated object, said two segments being arranged along the longitudinal extent of the second package part.

10. The package according to claim 9, wherein one segment of the second package part comprises two flap parts that are pivotal away from and toward one another along a bending edge that is oriented transverse to the longitudinal extent of said second package part.

11. The package according to claim 1, wherein the object has a shaft that is longer than the second package part.

12. The package according to claim 3, wherein the top part and bottom part of the package are formed of a plastic material and the at least one holding element is formed of an elastomerically deformable plastic cushion or sheet of material and where the plastic material of said top part and bottom part of said package is harder than the elastomerically deformable plastic of said at least one holding element, said at least one holding element being placed together with the top part and the bottom part.

13. The package according to claim 1 wherein said at least one holding part further defines a stop edge for aligning the object to be held with said package, said stop edge extending in the longitudinal direction of said package.

* * * * *